United States Patent
Merce-Vidal et al.

(10) Patent No.: US 6,410,582 B1
(45) Date of Patent: Jun. 25, 2002

(54) THIENYLAZOLYLALCOXYETHANAMINES, THEIR PREPARATION AND THEIR APPLICATION AS MEDICAMENTS

(75) Inventors: Ramon Merce-Vidal; Blas Andaluz-Mataro; Jordi Frigola-Constansa, all of Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 09/673,186

(22) PCT Filed: Apr. 15, 1999

(86) PCT No.: PCT/ES99/00098

§ 371 (c)(1),
(2), (4) Date: Oct. 12, 2000

(87) PCT Pub. No.: WO99/52525

PCT Pub. Date: Oct. 21, 1999

(30) Foreign Application Priority Data

Apr. 15, 1998 (ES) ................................ 9800793

(51) Int. Cl.$^7$ ...................... A61K 31/41; A61K 31/415; C07D 257/00; C07D 249/08; C07D 231/10
(52) U.S. Cl. ...................... 514/397; 514/383; 514/385; 514/382; 514/407; 514/408; 548/252; 548/266.6; 548/315.1; 548/375.1; 548/376.1; 548/527
(58) Field of Search .............................. 548/252, 266.6, 548/315.1, 527, 375.1, 376.1; 514/382, 383, 385, 397, 407, 408

(56) References Cited

U.S. PATENT DOCUMENTS 5,017,596 A * 5/1991 Colombo et al. ........... 548/378

FOREIGN PATENT DOCUMENTS

EP 0289380 11/1988

OTHER PUBLICATIONS

Mattioli, F. et al. "W–Dialkylaminoalkyl Ethers . . ." J. of Heterocyclic Chemistry, vol. 34, p. 963–968 (1997).

* cited by examiner

*Primary Examiner*—Floyd D. Higel
*Assistant Examiner*—Ebenezer Sackey
(74) *Attorney, Agent, or Firm*—Ladas & Parry

(57) ABSTRACT

The thienylazolylalkoxyethanamines (I) where R1 is a hydrogen atom, a halogen atom or a lower alkyl radical; R2, R3 and R4 represent, independently, a hydrogen atom or a lower alkyl radical; and Az represents a five-member nitrogenated heterocyclic aromatic group, N-methyl-substituted, that contains from one to three nitrogen atoms. They have analgesic activity in mammals, including humans. The compounds (I) can be obtained, for example, by reaction of a derivative of hydroxy-thienylazol (IV) with a derivative of a suitable N-(ethyl)amine. The compounds (IV) are useful intermediates in the synthesis of the compounds (I). The compounds (I) have an application in human and/or veterinary medicine.

6 Claims, No Drawings

THIENYLAZOLYLALCOXYETHANAMINES, THEIR PREPARATION AND THEIR APPLICATION AS MEDICAMENTS

This application is a 371 of PCT/ES 99/00098 filed on Apr. 15, 1999.

FIELD OF THE INVENTION

The present invention relates to new thienylazolylalkoxyethanamines of general formula (I), as well as their physiologically acceptable salts, to the procedures for their preparation, to their application as medicaments in human and/or veterinary therapy and to the pharmaceutical compositions that contain them.

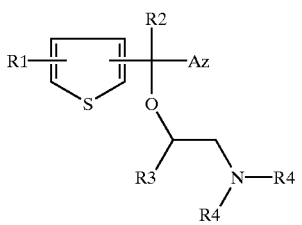
(I)

The new compounds object of the present invention can be used in the pharmaceutical industry as intermediates and for the preparation of medicaments.

The invention also relates to new derivatives of thienylazolylcarbinols, of general formula (IV), useful as starting materials or intermediates in the synthesis of the compounds of general formula (I).

BACKGROUND OF THE INVENTION

In our patent application EP 289380 we have described different derivatives of phenylpyrazolylcarbinols, of general formula (II)

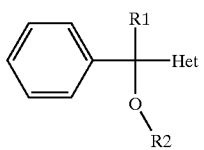
(II)

in which R1 represents a hydrogen atom or an alkyl group; R2 represents an aminoalkyl radical and Het represents an azol.

We have now discovered that substituting a benzene ring for a thiopheno ring gives rise to new compounds of general formula (I) that show some interesting biological properties. These properties make the new compounds particularly useful for use in human and/or veterinary therapy. The compounds object of this patent are useful as agents with analgesic activity.

DETAILED DESCRIPTION OF THE INVENTION

The present invention provides new compounds with potent analgesic activity.

The compounds object of the present invention correspond to the general formula (I)

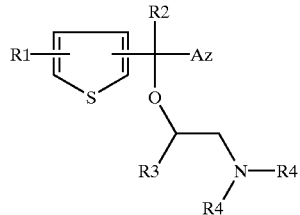
(I)

in which
R1 represents a hydrogen atom, a halogen atom or a lower alkyl radical; R2, R3 and R4 represent a hydrogen atom or a lower alkyl radical; and Az represents an nitrogenated heterocyclic aromatic five-member ring, N-methyl substituted, that contains from one to three atoms of nitrogen, of general formula (III)

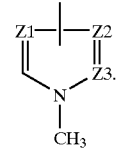

in which Z1, Z2 and Z3, independently, represent an atom of nitrogen or CH. with the condition that, at least, one of Z1, Z2 or Z3 is CH.

The term "lower alkyl" represents a linear or branched carbon chain that includes from 1 to 4 atoms of carbon, such as methyl, ethyl, propyl, isopropyl, butyl, isobutyl, sec-butyl and terc-butyl for example.

The new compounds of general formula (I) have at least one asymmetric carbon and so can be prepared enantiomerically pure or as racemates. The racemates of the compounds (I) can be resolved into their optical isomers by conventional methods, such as for example separation by chiral chromatography or fractionated crystallisation of their diastereoisomeric salts, which can be prepared by reaction of the compounds (I) with enantiomerically pure acids. Similarly, they can also be obtained by enantioselective synthesis using chiral precursors, preferably enantiomerically pure thienylazolylcarbinols.

The present invention relates equally to the physiologically acceptable salts of the compounds of general formula (I), in particular the addition salts of mineral acids such as hydrochloric, hydrobromic, phosphoric, sulphuric, nitric acids and organic acids such as citric, malic, fumaric, tartaric or its derivatives, p-toluensulphonic, methanesulphonic, canphosulfonic, etc., acids.

In an embodiment, the invention provides a compound of formula (I) wherein R1 is a halogen atom wherein said halogen atom represents a fluorine, chlorine, or bromine atom.

In a particular embodiment, the invention provides a compound of formula (I) selected from the following group:

[1] 5-{α-[2-(dimethylamino)ethoxy]-2-thienylmethyl}-1-methyl-1H-pyrazol;

[2] Citrate of 5-{α-[2-(dimethylamino)ethoxy]-2-thienylmethyl}-1-methyl-1H-pyrazol;

[3] 5-{α-[2-(dimethylamino)ethoxy]-3-thienylmethyl}-1-methyl-1H-pyrazol;

[4] 2-{α-[2-(dimethylamino)ethoxy]-2-thienylmethyl}-1-methyl-1H-imidazol;

[5] 5-{α-[2-(dimethylamino)ethoxy]-3-methyl-2-thienylmethyl}-1-methyl-1H-pyrazol;

[6] 5-{α-[2-(dimethylamino)ethoxy]-5-methyl-2-thienylmethyl}-1-methyl-1H-pyrazol;
[7] 5-{α-[2-(dimethylamino)ethoxy]-5-bromo-2-thienylmethyl}-1-methyl-1H-pyrazol;
[8] 5-{α-[2-(dimethylamino)ethoxy]-4-bromo-2-thienylmethyl}-1-methyl-1H-pyrazol;
[9] 5-{1-[2-(dimethylamino)ethoxy]-1-(2-thienyl)ethyl}-1-methyl-1H-pyrazol;
[10] (+)-5-{α-[2-(dimethylamino)ethoxy]-2-thienylmethyl}-1-methyl-1H-pyrazol;
[11] (−)-5-{α-[2-(dimethylamino)ethoxy]-2-thienylmethyl}-1-methyl-1H-pyrazol;
[12] Citrate of (+)-5-{α-[2-(dimethylamino)ethoxy]-2-thienylmethyl}-1-methyl-1H-pyrazol;
[13] Citrate of (−)-5-{α-[2-(dimethylamino)ethoxy]-2-thienylmethyl}-1-methyl-1H-pyrazol;
[14] D-toluoyltartrate of (+)-5-{α-[2-(dimethylamino)ethoxy]-2-thienylmethyl}-1-methyl-1H-pyrazol; and
[15] D-toluoyltartrate of (−)-5-{α-[2-(dimethylamino)ethoxy]-2-thienylmethyl}-1-methyl-1H-pyrazol.

The new derivatives of general formula (I), in which R1, R2, R3, R4 and Az have the aforementioned meaning, can be prepared according to the methods that are now described:

Method A

By reaction of a compound of general formula IV

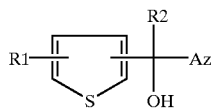

(IV)

with a compound of general formula V

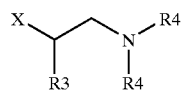

(V)

in which R1 to R4 and Az have the aforementioned meaning and X represents a halogen atom, preferably chlorine, or a leaving group such as tosiloxy or mesiloxy.

The reaction of the compound of general formula IV with a compound of general formula V in the form a base or salt, is carried out in the presence of an appropriate solvent such as a hydrocarbon such as benzene or toluene for example or in halogenated solvents such as chloromethane or tetrachloromethane or in ethers such as tetrahydrofurane or in aprotic dipolar solvents such as dimethylsulphoxide or dimethylformamide.

The reaction is preferably carried out in the presence of an appropriate base such as the mineral bases such as sodium hydroxide or potassium hydroxide or the carbonates or bicarbonates of sodium or potassium for example.

The reaction is preferably carried out in the presence of a phase transfer catalyst such as tetrabutylamonium bromide, triethylbenzylamonium chloride or crown ethers, in a temperature range lying between room temperature and the solvent reflux temperature.

Method B

By reaction of a compound of general formula VI

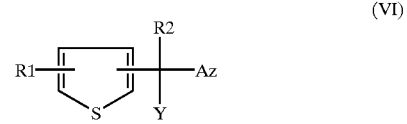

(VI)

with a compound of general formula VII

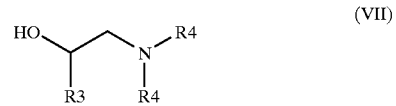

(VII)

in which R1 to R4 and Az have the aforementioned meaning and Y represents a halogen atom, preferably chlorine, a leaving group such as tosiloxy or mesiloxy or a hydroxyl radical.

The reaction of the compound of general formula VI with a compound of general formula VII in the form a base or salt, is carried out in the presence of an appropriate solvent such as a hydrocarbon such as benzene or toluene for example or in halogenated solvents such as chloromethane or tetrachloromethane or in ethers such as tetrahydrofurane or in aprotic dipolar solvents such as dimethylsulphoxide or dimethylformamide.

The reaction is preferably carried out in the presence of an appropriate base such as the mineral bases such as sodium hydroxide or potassium hydroxide or the carbonates or bicarbonates of sodium or potassium for example.

The reaction can be carried out in the presence of a phase transfer catalyst such as tetrabutylamonium bromide, triethylbenzylamonium chloride or the crown ethers, in a temperature range lying between room temperature and the solvent reflux temperature.

When Y represents a hydroxyl radical the reaction is preferably carried out in the presence of a strong acid such as sulphuric acid, in or not in the presence of an appropriate solvent such as benzene and in a temperature range lying between room temperature and the reflux temperature of the solvent.

Method C

By reduction of a compound of general formula VIII

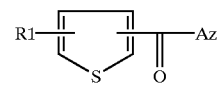

(VIII)

in which R1 and Az have the aforementioned meaning, whereupon an intermediate compound is obtained of general formula IV in which R1 and Az have the aforementioned meaning and R2 represents a hydrogen atom.

The reduction is carried out with hydrides such as aluminium hydride and lithium hydride in an appropriate solvent such as for example an ether such as tetrahydrofurane, dimethylether or dioxane, or else with boron hydride and sodium in an alcohol such as methanol or ethanol, or else with hydrogen in an appropriate solvent such as an alcohol, hydrocarbon or ether with an appropriate catalyst such as Raney nickel, platinum oxide or palladium. In the case of hydrogenation the pressure of hydrogen preferably lies between 1.01 and 20.2 bars (1 and 20 atmospheres), the temperatures vary between 20 and 100° C. and the reaction time between 1 and 24 hours.

Method D

By addition of organometallic compounds to carbonyl compounds, for example, by the reaction of a carbonyl compound of general formula IX

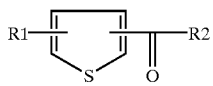
(IX)

with organometallic reagents of general formula Az-M (Method D-1) or else (Method D-2), by reaction of a carbonyl compound of general formula X

X with organometallic reagents of general formula XI

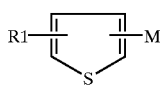
XI in which R1, R2 and Az have the aforementioned meaning and M represents an atom of lithium or the MgX function of the Grignard reagents, where X represents a halogen, preferably a bromine atom, whereupon an intermediate compound is obtained of general formula IV in which R1, R2 and Az have the aforementioned meaning.

Method E

The salts of the compounds of general formula (I) are prepared by the reaction of a compound of general formula (I) with an inorganic acid such as hydrochloric acid, hydrobromic acid, phosphoric acid, sulphuric acid, nitric acid or with organic acids such as citric, malic, fumaric, tartaric or its derivatives, p-toluensulphonic, methansulphonic, etc., acid, in an appropriate solvent such as methanol, ethanol, ethyl ether, ethyl acetate, acetonitrile or acetone, obtaining the corresponding salts with the usual techniques of precipitation or crystallisation.

Method F

The preparation of the compounds of general formula (I) in enantiomerically pure form in accord with the present invention is based on the optical resolution of a racemic amine by the employment of an optically active acid in which at least one of the enantiomers is capable of forming a diastereoisomeric salt between an enantiomer of the compound of general formula (I) and an enantiomer of a chiral acid, such as tartaric acid and its dibenzoyltartaric, ditoluyltartaric, and other derivatives, malic acid, mandelic acid and their derivatives, canphorsulphonic acid and its derivatives, among others. The chiral acid employed can be used either on its own or forming part of a mixtures with other inorganic and organic acids, either chiral or non-chiral, such as hydrochloric acid, p-toluensulphonic, methansulphonic acid, in molar ratios that range from 0.5% to 50%. Preferably, the chiral acid is selected from (−)-ditoluoyl-L-tartaric acid and (+)-ditoluoyl-D-tartaric acid, either on their own or else mixed, individually, with p-toluensulphonic acid.

The procedure is carried out in an appropriate solvent such as water, acetone, acetonitrile, methanol, ethanol, isopropanol, ter-butanol, dichloromethane, chloroform, carbon tetrachloride, dimethylformamide, dimethylsulphoxide, ethyl acetate, tetrahydrofurane, 1,4-dioxane, ethylenglycol, 1,2-dimethoxyethane, and in general any solvent susceptible to being used in a chemical process. The procedure can be carried out in a temperature range lying between −20° C. and the reflux temperature of the reaction mixture. The diastereoisomeric salt, once formed, can be separated by conventional methods such as fractionated crystallisation, chromatography and other methods. This resolution procedure can be used to resolve racemic mixtures of a compound of general formula (I) (that is to say, those mixtures in which the two enantiomers are found in a 1:1 ratio) or to resolve non-racemic mixtures of a compound of general formula (I) (mixtures in which one of the enantiomers is the major component), obtained by any physical or chemical method.

The invention provides pharmaceutical compositions that comprise, as well as an acceptable pharmaceutical excipient, at least one compound of general formula (I) or one of their physiologically acceptable salts. The invention also relates to the use of a compound of general formula (I) and its physiologically acceptable salts in the manufacture of a medicament with analgesic activity.

The invention also relates to new derivatives of thienylazolylcarbinols, of general formula (IV)

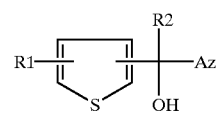
(IV)

in which

R1 is a hydrogen or halogen atom, or an alkyl radical of 1 to 4 carbon atoms;

R2 is an atom of hydrogen or an alkyl radical of 1 to 4 carbon atoms; and

Az is N-methylpyrazol.

Compounds of formula (IV) are useful as starting materials or intermediates in the synthesis of the compounds of general formula (I).

In a particular embodiment, the invention provides a compound of formula (IV) selected from the following group:

[16] 5-(α-hydroxy-2-thienylmethyl)-1-methyl-1H-pyrazol;
[17] 5-(α-hydroxy-3-methyl-2-thienylmethyl)-1-methyl-1H-pyrazol;
[18] 5-(α-hydroxy-5-methyl-2-thienylmethyl)-1-methyl-1H-pyrazol;
[19] 5-(α-hydroxy-5-bromo-2-thienylmethyl)-1-methyl-1H-pyrazol;
[20] 5-(α-hydroxy-4-bromo-2-thienylmethyl)-1-methyl-1H-pyrazol; and
[21] 5-[1-hydroxy-1-(2-thienyl)ethyl]-1-methyl-1H-pyrazol.

In the following examples the preparation of new compounds according to the invention is indicated. Also described are some ways of use typical for the different fields of application, as well as galenic formulas applicable to the compounds object of the invention.

The examples that are now indicated, are for illustrative purposes, and should in no way limit the extent of the invention.

Method A

EXAMPLE 1

Preparation of 5-{α-[2-(dimethylamino)ethoxy]-2-thienylmethyl}-1-methyl-1H-pyrazol A mixture of 18 g of 5-(α-hydroxy-2-thienylmethyl)-1-methyl-1H-pyrazol, 26.7 g of N-(2-chloroethyl)

dimethylamine chlorohydrate, 150 ml of NaOH 50%, 300 ml of toluene and 1 g of tetrabutylamonium bromide were shaken under reflux for 24 hours. After cooling, the organic phase was separated, washed with water, and dried over sodium sulphate and evaporated to dryness. 21.4 g (87%) of 5-{α-[2-(dimethylamino)ethoxy]-2-thienylmethyl}-1-methyl-1H-pyrazol were obtained in the form of an oil.

The compounds identified by the examples 3 to 9 are obtained by the same method of preparation described for example I and the data for the identification of the products are presented in Table 1.

Method B

EXAMPLE 1

Preparation of 5-{α-[2-(dimethylamino)ethoxy]-2-thienylmethyl}-1-methyl-1H-pyrazol A mixture of 8.7 g of 5-(α-hydroxy-2-thienylmethyl)-1-methyl-1H-pyrazol, 6.23 of 2-(dimethylamino)ethanol and 0.5 ml of sulphuric acid concentrated in 80 ml of toluene were shaken under reflux connected to a Dean-Stark for 8 hours. After cooling, the organic phase is separated, washed with sodium bicarbonate and water, and dried over sodium sulphate and evaporated to dryness. 4.7 g (40%) of 5-{α-[2-(dimethylamino)ethoxy]-2-thienylmethyl}-1-methyl-1H-pyrazol were obtained.

The compounds identified by examples 3 to 9 are obtained by the same preparation method as that described in example 1 and the data for the identification of the products are presented in table 1.

Method C

EXAMPLE 16

Preparation of 5-(α-hydroxy-2-thienylmethyl)-1-methyl-1H-pyrazol 3.2 g of boron hydride and sodium are added to a solution of 3.2 g of 5-(α-oxo-2-thienylmethyl)-1-methyl-1H-pyrazol in 100 ml of methanol. The mixture is shaken for 1 hour and water added. Next, the solution is extracted with chloroform, washed with water and dried over sodium sulphate and evaporated to dryness. 2.9 g (90%) of an oil is obtained which is 5-(α-hydroxy-2-thienylmethyl)-1-methyl-1H-pyrazol.

The compounds identified by the examples 17 to 20 are obtained by the same preparation method described for example 16 and the data for the identification of the products are shown in Table 3.

Method D

EXAMPLE 16

Preparation of 5-(α-hydroxy-2-thienylmethyl)-1-methyl-1H-pyrazol 100 ml of a solution of 1.6 M butilite in hexane are added dropwise to a solution, cooled to −5° C. and maintained under a nitrogen atmosphere, of 11.6 g of N-methylpyrazol in 100 ml of tetrahydrofurane anhydride. To the resulting suspension, a solution of 15.9 g of 2-thiophenocarboxaldehyde in tetrahydrofurane anhydride is added dropwise at a temperature of −78° C. The reaction is shaken for 4 hours, and the temperature allowed to rise to −20° C. before hydrolysing with 100 ml of water. The tetrahydrofurane is evaporated off and the aqueous phase extracted with chloroform. The organic phase is washed with water, and dried over sodium sulphate and evaporated to dryness. The resulting crude product is suspended in petrol ether and decanted. 23.5 g (85%) of an oil are obtained, this oil being 5-(α-hydroxy-2-thienylmethyl)-1-methyl-1H-pyrazol.

The compounds identified by the examples 17 to 21 are obtained by the same preparation method described for example 16 and the data for the identification of the products are shown in Table 3.

Method E

EXAMPLE 2

Preparation of the citrate of 5-{α-[2-(dimethylamino)ethoxy]-2-thienylmethyl}-1-methyl-1H-pyrazol A solution of 16.2 g of monohydrate citric acid in 40 ml of ethanol are added to a solution of 20.5 g of 5-{α-[2-(dimethylamino)ethoxy]-2-thienylmethyl}-1-methyl-1H-pyrazol in 50 ml of ethanol. 31 g (88%) of citrate of 5-{α-[2-(dimethylamino)ethoxy]-2-thienylmethyl}-1-methyl-1H-pyrazol precipitate out as a white solid with a melting point of 115–116° C. The data for the identification of the product are presented in Table 1.

The compounds identified by the examples 12 and 13 are obtained by the same preparation method described for example 2 and the data for the identification of the products are presented in Table 2.

Method F

EXAMPLE 11

Preparation of (−)-5-{α-[2-(dimethylamino)ethoxy]-2-thienylmethyl}-1-methyl-1H-pyrazol 12.09 g of (−)-di-O,O'-p-toluoyl-L-tartaric acid are added to a solution of 16.6 g of (±)-5-{α-2[2-(dimethylamino)ethoxy]-2-thienylmethyl}-1-methyl-1H-pyrazol in 63 ml of isopropanol. The solution is heated and 5.95 g of prtoluen-sulphonic acid monohydrate are added. Next, the solution is allowed to cool and 158 ml of ethyl ether added to it. 9.4 g of L-ditoluoyltartrate precipitate out as a white solid whose diastereoisomeric ratio determined by $^1$H-NMR, capillary electrophoresis and HPLC in an AGP (α-glycoprotein) chiral column is (94:6). 9.2 g of this solid are treated with 0.16 g (0.06 equivalents) of p-toluensulphonic acid monohydrate and re-crystallisation carried out in 44 ml of isopropanol. 6.8 g of L-ditoluoyltartrate (95.4:4.6) are obtained. The following re-crystallisation in 30 ml of isopropanol with 91.3 mg (0.046 equivalents) of p-toluensulphonic acid monohydrate leads to 5.55 g of salt (97.7:2.3). A final re-crystallisation in isopropanol with 38.1 mg (0.023. equivalents) of p-toluensulphonic acid monohydrate yields 4.34 g of L-ditoluoyltartrate of (−)-5-{-{α-[2-(dimethylamino)ethoxy]-2-thienylmethyl}-1-methyl-1H-pyrazol (example 15) as a white solid with a m.p. of 130–131° C.; an enantiomeric purity of 98.5% (97% ee) as determined by HPLC on an AGP (α-glycoprotein) chiral column; $[α]_D$=−85.4 (c=2.0 MeOH). By alkanisation of the L-ditoluoyltartrate salt of (−)-5-{-{α-[2-(dimethylamino)ethoxy]-2-thienylmethyl}-1-methyl-1H-pyrazol, the product (−)-5-{- {α-[2-(dimethylamino)ethoxy]-2-thienylmethyl}-1-methyl-1H-pyrazol is obtained in quantitative fashion $[α]_D$=−31.8 (c=2.0 MeOH).

The compounds identified by the examples 10 and 14 are obtained by the same preparation method described for examples 11 and 15 and the data for the identification of the products are presented in Table 2.

TABLE 1

Tfn—C(R2)(Az)—O—CH(R3)—CH2—N(R4)(R4)

| Ex. | Az | Tfn | R2 | R3 | R4 | Base or salt | m.p. (° C.) | 1H-NMR (MHz) (solvent)δ | IR cm−1 |
|---|---|---|---|---|---|---|---|---|---|
| 1 | 1-methyl-5-pyrazolyl | 2-thienyl | H | H | CH3 | Base | Oil | (300 MHz) (CDCl3) 2.24(s, 6H), 2.54(t, J=6Hz, 2H), 3.58(m, 2H), 3.79(s, 3H), 5.76(s, 1H), 6.17(d, J=1.8Hz, 1H), 6.83(m, 1H) 6.93(m, 1H), 7.28(m, 1H), 7.38(d, J=1.8Hz, 1H) | (film) 2944, 2863, 2821, 2771, 1457, 1100, 1092, 1066, 1056, 1042, 705, 651 |
| 2 | 1-methyl-5-pyrazolyl | 2-thienyl | H | H | CH3 | Citrate | 115–116 | (300 MHz) (DMSO-d6) 2.51(AB system, J=15 Hz, 2H), 2.71(AB system, J=15Hz, 2H), 2.66(s, 6H), 3.18(m, 2H), 3.70–3.80(br, 5H, (δ=3.74, s)), 6.07(s, 1H), 6.16(s, 1H), 7.01(m, 1H), 7.10 (m, 1H), 7.34(s, 1H), 7.57(m, 1H) | (KBr) 3300–2300 (broad), 1732, 1589, 1475, 1398, 1380, 1356, 1220, 1203, 1183 |
| 3 | 1-methyl-5-pyrazolyl | 3-thienyl | H | H | CH3 | Base | oil | (300 MHz) (CDCl3) 2.24(s, 6H), 2.54(t, J=6Hz, 2H), 3.56(m, 2H), 3.77(s, 3H), 5.59(s, 1H), 6.08(d, J=1.8Hz, 1H), 6.99(dd, J=5Hz, J'=1.2 Hz, 1H), 7.19(m, 1H), 7.30(dd, J=5Hz, J'=3Hz, 1H), 7.37(d, J=1.8Hz, 1H). | (film) 2942, 2819, 2769, 1456, 1103, 783, 753 |
| 4 | 1-methyl-2-imidazolyl | 2-thienyl | H | H | CH3 | Base | oil | (300 MHz) (CDCl3) 2.24(s, 6H), 2.56(m, 2H), 3.54(m, 1H), 3.56(s, 3H), 3.67(m, 1H), 5.90(s, 1H), 6.77(m, 1H), 6.85(d, J=1.2Hz, 1H), 6.93 (m, 1H), 6.98(d, J=1.2Hz, 1H), 7.27(m, 1H) | (film) 2943, 2864, 2820, 2770, 1496, 1456, 1278, 1103, 1056, 772, 702 |
| 5 | 1-methyl-5-pyrazolyl | 3-methyl-2-thienyl | H | H | CH3 | base | oil | (300 MHz) (CDCl3) 2.14(s, 3H), 2.23(s, 6H), 2.54(t, J=6Hz, 2H), 3.59(m, 2H), 3.84(s, 3H), 5.74(s, 1H), 6.04(s, 1H), 6.80(d, J=5.0Hz, 1H), 7.18(d, J=.50Hz, 1H), 7.33(s, 1H) | (film) 2944, 2865, 2821, 2772, 1455, 1100, 1092, 1067, 1055, 1042, 782, 715 |
| 6 | 1-methyl-5-pyrazolyl | 5-methyl-2-thienyl | H | H | CH3 | base | oil | (300 MHz) (CDCl3) 2.24(s, 6H), 2.43(s, 3H), 2.53(t, J=6Hz, 2H), 3.56(m, 2H), 3.80(s, 3H), 5.65(s, 1H), 6.17(d, J=1.5Hz, 1H), 6.62(d, J=2.4Hz 1H), 7.37(d, J=1.5Hz, 1H) | (film) 2944, 2863, 2820, 2772, 1456, 1286, 1101, 1092, 1067, 1055, 1042, 798, 783, 762, 652 |
| 7 | 1-methyl-5-pyrazolyl | 5-bromo-2-thienyl | H | H | CH3 | base | oil | (300 MHz) (CDCl3) 2.25(s, 6H), 2.55(t, J=6Hz, 2H), 3.57(m, 2H), 3.80(s, 3H), 5.68(s, 1H), 6.20(d, J=2.1Hz, 1H), 6.56(d, J=4Hz 1H), 6.90(d, J=4Hz, 1H), 7.40 (d, J=2.1Hz, 1H) | (film) 2943, 2864, 2821, 2772, 1441, 1101, 1093, 1066, 1055, 1042, 968, 793, 761, 651. |
| 8 | 1-methyl-5-pyrazolyl | 4-bromo-2-thienyl | H | H | CH3 | base | Oil | (300 MHz) (CDCl3) 2.23(s, 6H), 2.53(t, J=5.7 Hz, 2H), 3.57(m, 2H), 3.78(s, 3H), 5.72(s, 1H), 6.18(d, J=2.1Hz, 1H), 6.74(d, J=1.5Hz, 1H), 7.19(d, J=1.5Hz, 1H), 7.39(d, J=2.1Hz, 1H) | (film) 2994, 2864, 2821, 2772, 1456, 1344, 1101, 1093, 1056, 1042, 780 |
| 9 | 1-methyl-5-pyrazolyl | 2-thienyl | CH3 | H | CH3 | base | oil | (300 MHz) (CDCl3) 1.91(s, 3H), 2.26(s, 6H), 2.52(m, 2H), 3.17(m, 1H), 3.59(m, 1H), 3.63(s, 3H), 6.31(d, J=1.5Hz, 1H), 6.58(m, 1H), 6.88 (m, 1H), 7.21(m, 1H), 7.41(d, J=1.5Hz, 1H) | (film) 2940, 2819, 2770, 1456, 1369, 1235, 1108, 1041, 930, 699 |

TABLE 2

$$\text{Tfn} - \underset{\underset{\underset{H_3C}{\overset{|}{N}}-CH_3}{\overset{|}{O}}}{\overset{R2}{\overset{|}{C}}} - Az$$

| Example | Az | Tfn | R2 | Base or salt | Optical isomer | Enantiomerical purity % | Specific rotation | Melting point (° C.) |
|---|---|---|---|---|---|---|---|---|
| 10 | 1-methyl-3-methylpyrazol-5-yl | 5-methylthien-2-yl | H | Base | (+) | 99 | +31.8 (c = 2.0 CH$_2$Cl$_2$) | Oil |
| 11 | 1-methyl-3-methylpyrazol-5-yl | 5-methylthien-2-yl | H | Base | (+) | 98.5 | −31.8 (c = 2.0 CH$_2$Cl$_2$) | Oil |
| 12 | 1-methyl-3-methylpyrazol-5-yl | 5-methylthien-2-yl | H | Citrate | (+) | 99 | +2.8 (c = 2.0 CH$_2$Cl$_2$) | 121–122 |
| 13 | 1-methyl-3-methylpyrazol-5-yl | 5-methylthien-2-yl | H | Citrate | (−) | 98.5 | −2.3 (c = 2.0 CH$_2$Cl$_2$) | 121–122 |
| 14 | 1-methyl-3-methylpyrazol-5-yl | 5-methylthien-2-yl | H | (D)-ditoluoyl tartrate | (+) | 99 | +87.5 (c = 2.0 CH$_2$Cl$_2$) | 130–131 |
| 15 | 1-methyl-3-methylpyrazol-5-yl | 5-methylthien-2-yl | H | (L)-ditoluoyl tartrate | (−) | 98.5 | −85.4 (c = 2.0 CH$_2$Cl$_2$) | 130–131 |

TABLE 3

$$\text{Tfn} - \underset{\underset{OH}{\overset{|}{}}}{\overset{R2}{\overset{|}{C}}} - Az$$

| Example | Az | Thiopheno | R2 | Base or salt | Melting point (° C.) | $^1$H-NMR (MHz) (Solvent)δ | IR, cm$^{-1}$ |
|---|---|---|---|---|---|---|---|
| 16 | 1-methyl-3-methylpyrazol-5-yl | 5-methylthien-2-yl | H | Base | Oil | (300 MHz) (CDCl$_3$) 3.67(s, 3H), 5.00 (d, J=4.5Hz, 1H), 6.06(d, J=4.5Hz, 1H), 6.16(s, 1H), 6.84(m, 1H), 6.94 (m, 1H), 7.23(s, 1H), 7.27(d, J=5.1 Hz, 1H) | (film) 3210 (broad), 1433, 1400, 1284, 1201, 1055, 1037, 1003, 781, 760, 706 |

TABLE 3-continued $$\text{Tfn} - \underset{\underset{\text{OH}}{|}}{\overset{\overset{R2}{|}}{C}} - \text{Az}$$

| Example | Az | Thiopheno | R2 | Base or salt | Melting point (° C.) | $^1$H-NMR (MHz) (Solvent)δ | IR, cm$^{-1}$ |
|---|---|---|---|---|---|---|---|
| 17 | 1,5-dimethylpyrazol-3-yl | 2-methyl-3-thienyl | H | Base | 109–111 | (300 MHz) (CDCl$_3$) 2.19(s, 3H), 2.63 (d, J=4.5Hz, 1H), 3.82(s, 3H), 6.13 (d, J=4.5Hz, 1H), 6.16(d, J=1.5Hz, 1H), 6.83(d, J=5.1Hz, 1H), 7.20(d, J=5.1Hz, 1H), 7.37(d, J=1.5Hz, 1H) | (KBr) 3199 (broad), 1400, 1282, 1200, 1060, 998, 940, 796, 776, 732 |
| 18 | 1-methylpyrazol-3-yl | 3-methyl-5-thienyl | H | Base | 131–132 | (300 MHz) (CDCl$_3$) 2.46(s, 3H), 2.79 (d, J=4.6Hz, 1H), 3.80(s, 3H), 6.04 (d, J=4.6Hz, 1H), 6.25(d, J=1.8Hz, 1H), 6.62(d, J=3.3Hz, 1H), 6.70(d, J=3.3Hz, 1H), 7.39(d, J=1.8Hz, 1H) | (KBr) 3163 (broad), 3100, 1282, 1206, 1025, 1010, 801, 788 |
| 19 | 1-methylpyrazol-3-yl | 3-bromo-5-thienyl | H | Base | 107–109 | (300 MHz) (CDCl$_3$) 3.76(s, 3H), 3.86 (br, 1H), 6.02(s, 1H), 6.20(d, J=1.8 Hz), 6.61(d, J=4.0Hz, 1H), 6.91(d, J=4.0Hz, 1H), 7.32(d, J=1.8Hz, 1H) | (KBr) 3170 (broad), 3104, 1440, 1395, 1205, 1181, 1025, 1011, 966, 800, 791 |
| 20 | 1-methylpyrazol-3-yl | 4-bromo-5-methyl-2-thienyl | H | Base | 95–6 | (300 MHz) (CDCl$_3$) 3.60(br, 1H), 3.78(s, 3H), 6.08(s, 1H), 6.20(d, J=1.8Hz, 1H), 6.80(s, 1H), 7.21(s, 1H), 7.35(d, J=1.8Hz, 1H) | (KBr) 3112 (broad), 1397, 1343, 1205, 1182, 1132, 1052, 823, 795, 768 |
| 21 | 1-methylpyrazol-3-yl | 2-thienyl | CH$_3$ | Base | 130–131 | (300 MHz) (CDCl$_3$) 2.00(s, 3H), 3.27 (br, 1H), 3.68(s, 3H), 6.26(d, J=2.0 Hz, 1H), 6.68 8m, 1H), 6.91(m, 1H), 7.23(m, 1H), 7.32(d, J=2.0Hz, 1H) | (KBr) 3264 (broad), 1384, 1221, 1159, 1114, 802, 779, 707 |

Analgesic Activity: Inhibition of Contortions Induced by Phenylbenzoquinone in Mice The method described by Siegmund (E. Siegmund, et al, Proc. Exp. Biol. Med., 1957, 95, 729) has been used. Male Swiss mice are used, weighing between 17 and 22 grams and in groups of at least four animals.

The contortions are induced by injecting i.p. phenyl-p-benzoquinone (25 ml/Kg of a solution of 0.02% ethanol/water—5% v/v—with Evans blue at a mixing ratio of 0.1% p/v). The contortions are counted for 15 minutes after the moment of the injection. The products to be tested are suspended in Arabic gum (5% p/v) and distilled water and administered orally, at a dosage of 160 mg/Kg, 60 minutes before the phenylbenzoquinone injection. The inhibition of contortions produced by each product is determined, taking the contortions of a group of animals given a control as a reference. These animals only receive the vehicle orally, 60 minutes before administration of phenylbenzoquinone.

The results obtained with some of the products are indicated by way of example in table 4.

TABLE 4

Analgesic activity: Inhibition of contortions induced by phenylbenzoquinone in mice
Dosage of product: 160 mg/Kg, oral administration

| Product | % Inhibition of contortions |
|---|---|
| Example 1 | 71 |
| Example 2 | 65 |
| Example 5 | 45 |
| Example 9 | 37 |
| Example 12 | 52 |
| Example 13 | 87 |
| Acetylsalicylic acid | 51 |
| N-acetyl-p-aminophenol | 34 |

Taking into account the good pharmacodynamic properties, the derivatives of thienylazolylalkoxyethanamine according to the invention can be used in a satisfactory fashion in human and animal therapy, in particular in the treatment of pain of moderate to strong intensity, such as sciatic, lumbago, dorsalgias, sprains, fractures, dislocations, post-operation pain, toothache, etc.

In human therapy, the administration dosage of the compounds of the present invention varies as a function of the seriousness of the affliction to be treated. Normally this dosage will lie between 100 and 400 mg/day. The compounds of the invention are administered in the form of capsules, as tablets, or injectable solutions or suspensions, for example.

Next, by way of example, two particular galenic forms of the compounds object of the present invention will be presented.

Pharmaceutical Formulations

Example of an injectable formula (i.m, i.v.):

| | |
|---|---|
| Example 2 | 20 mg |
| Sodium chloride | sufficient quantity |
| HCl 0.1 N or NaOH 0.1 N | sufficient quantity |
| Water for injection, to | 1 ml |

Example of a formula for a tablet

| | |
|---|---|
| Example 2 | 30 mg |
| Corn starch | 46 mg |
| Colloidal silicon dioxide | 1.15 mg |
| Magnesium stearate | 1.15 mg |
| Povidone K-90 | 4.60 mg |
| Pre-gellatinised starch | 4.60 mg |
| Micro-crystalline cellulose | 23 mg |
| Lactose, to | 230 mg |

What is claimed is:

1. A thienylazolylalkoxyethanamine of the formula (I)

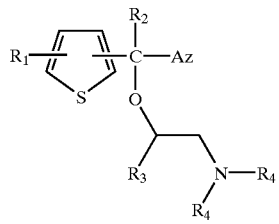

in which

R1 is a hydrogen or halogen atom, or an alkyl radical of 1 to 4 carbon atoms;

R2, R3 and R4 represent, independently, an atom of hydrogen or an alkyl radical of 1 to 4 carbon atoms; and Az represents a nitrogenated heterocyclic aromatic five-member ring, N-methyl substituted, that contains from one to three atoms of nitrogen, of formula (III)

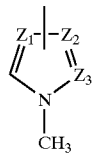

in which Z1, Z2 and Z3, independently, represent an atom of nitrogen or CH, or a physiologically acceptable salt thereof.

2. A compound according to claim 1, in which the halogen atom represents a fluorine, chlorine, or bromine atom.

3. A compound according to claim 1, selected from the following group:

[1] 5-{α-[2-(dimethylamino)ethoxy]-2-thienylmethyl}-1-methyl-1H-pyrazol;

[2] Citrate of 5-{α-[2-(dimethylamino)ethoxy]-2-thienylmethyl}-1-methyl-1H-pyrazol;

[3] 5-{α-[2-(dimethylamino)ethoxy]-3-thienylmethyl}-1-methyl-1H-pyrazol;

[4] 2-{α-[2-(dimethylamino)ethoxy]-2-thienylmethyl}-1-methyl-1H-imidazol;

[5] 5-{α-[2-(dimethylamino)ethoxy]-3-methyl-2-thienylmethyl}-1-methyl-1H-pyrazol;

[6] 5-{α-[2-(dimethylamino)ethoxy]-5-methyl-2-thienylmethyl}-1-methyl-1H-pyrazol;

[7] 5-{α-[2-(dimethylamino)ethoxy]-5-bromo-2-thienylmethyl}-1-methyl-1H-pyrazol;

[8] 5-{α-[2-(dimethylamino)ethoxy]-4-bromo-2-thienylmethyl}-1-methyl-1H-pyrazol;

[9] 5-{1-[2-(dimethylamino)ethoxy]-1-(2-thienyl)ethyl}-1-methyl-1H-pyrazol;

[10] (+)-5-{α-[2-(dimethylamino)ethoxy]-2-thienylmethyl}-1-methyl-1H-pyrazol;

[11] (−)-5-{α-[2-(dimethylamino)ethoxy]-2-thienylmethyl}-1-methyl-1H-pyrazol;

[12] Citrate of (+)-5-{α-[2-(dimethylamino)ethoxy]-2-thienylmethyl}-1-methyl-1H-pyrazol;

[13] Citrate of (−)-5-{α-[2-(dimethylamino)ethoxy]-2-thienylmethyl}-1-methyl-1H-pyrazol;

[14] D-toluoyltartrate of (+)-5-{α-[2-(dimethylamino)ethoxy]-2-thienylmethyl}-1--methyl-1H-pyrazol; and

[15] D-toluoyltartrate of (−)-5-{α-[2-(dimethylamino)ethoxy]-2-thienylmethyl}-1-methyl-1H-pyrzaol.

4. A process for obtaining a compound of thienylazolylalkoxyethanamine of formula (I), according to claim 1, which comprises reacting a compound of formula (IV)

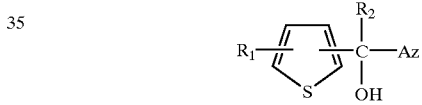

in which R1, R2 and Az have the meaning indicated in claim 1;

with a compound of formula (V)

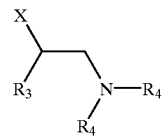

in which R3 and R4 have the meaning indicated in claim 1, and X represents a halogen atom or a leaving group.

5. A pharmaceutical composition which it contains, at least, one compound of thienylazolylalkoxyethanamine of formula (I), or one of its physiologically acceptable salts, according to claim 1 and a pharmaceutically acceptable excipient.

6. A method of inducing analgesia in a mammal which comprises administering to said mammal and analgesically effective amount of a compound as claimed in claim 1.

* * * * *